United States Patent
Vardon

(10) Patent No.: US 12,351,768 B2
(45) Date of Patent: Jul. 8, 2025

(54) RENEWABLE CO-SOLVENTS FOR THERMOCHEMICAL BIO-OIL PROCESSING

(71) Applicant: Alliance for Sustainable Energy, LLC, Golden, CO (US)

(72) Inventor: Derek Richard Vardon, Lakewood, CO (US)

(73) Assignee: Alliance for Sustainable Energy, LLC, Golden, CO (US)

( * ) Notice: Subject to any disclaimer, the term of this patent is extended or adjusted under 35 U.S.C. 154(b) by 0 days.

(21) Appl. No.: 18/290,903

(22) PCT Filed: Jul. 27, 2022

(86) PCT No.: PCT/US2022/038475
§ 371 (c)(1),
(2) Date: Jan. 22, 2024

(87) PCT Pub. No.: WO2023/009597
PCT Pub. Date: Feb. 2, 2023

(65) Prior Publication Data
US 2024/0352362 A1 Oct. 24, 2024

Related U.S. Application Data

(60) Provisional application No. 63/227,564, filed on Jul. 30, 2021.

(51) Int. Cl.
C10L 1/02 (2006.01)
C07C 5/10 (2006.01)
C07C 29/145 (2006.01)

(52) U.S. Cl.
CPC ...... *C10L 1/02* (2013.01); *C07C 5/10* (2013.01); *C07C 29/145* (2013.01)

(58) Field of Classification Search
CPC . C07C 29/145; C07C 5/10; C10L 1/02; C10L 1/125; C10L 1/1824; C10L 1/1881; C10L 2290/02
See application file for complete search history.

(56) References Cited

U.S. PATENT DOCUMENTS

| | | |
|---|---|---|
| 10,486,141 B2 | 11/2019 | Vardon et al. |
| 11,420,912 B2 | 8/2022 | Vardon et al. |
| 2008/0070825 A1 | 3/2008 | Bertram et al. |

(Continued)

OTHER PUBLICATIONS

International Search Report and Written Opinion for International (PCT) Application No. PCT/US22/38475, date of mailing Nov. 22, 2022, pp. 1-10.

(Continued)

*Primary Examiner* — Latosha Hines
(74) *Attorney, Agent, or Firm* — Michael A. McIntyre

(57) ABSTRACT

Treating pyrolysis oil to yield a liquid fuel or liquid fuel precursor includes combining the pyrolysis oil with one or more co-solvents to yield a mixture, and hydrotreating the mixture to yield the liquid fuel or liquid fuel precursor. The co-solvent can include one or more alcohols. The liquid fuel can be a transportation fuel, such as gasoline, diesel fuel, jet fuel, or marine fuel. The liquid fuel precursor can be a transportation fuel precursor, such as a gasoline precursor, a diesel fuel precursor, a jet fuel precursor, or a marine fuel precursor.

15 Claims, 10 Drawing Sheets

(56) References Cited

U.S. PATENT DOCUMENTS

| | | | |
|---|---|---|---|
| 2012/0035404 A1* | 2/2012 | Alegria | C10G 3/42 |
| | | | 585/240 |
| 2014/0059921 A1 | 3/2014 | Weaver et al. | |
| 2018/0291276 A1* | 10/2018 | Gangwal | C10G 45/02 |
| 2019/0185884 A1 | 6/2019 | Foody | |
| 2019/0338194 A1 | 11/2019 | Brodeur-Campbell et al. | |

OTHER PUBLICATIONS

International Preliminary report on Patentability for International (PCT) Application No. PCT/US22/38475, mail date Feb. 8, 2024, pp. 1-7.

Han et al., "Ternary Phase Diagram of Water/Bio-Oil/Organic Solvent for Bio-Oil Fractionation", Energy & Fuels, 2020, vol. 34, No. 12, pp. 16250-16264.

Kokal et al., "Crude Oil Emulsions: A State-Of-The-Art Review", SPE Production & Facilities, Feb. 2005, vol. 20, No. 1, pp. 5-13.

Perkins et al., "Process development status of fast pyrolysis technologies for the manufacture of renewable transport fuels from biomass", Renewable and Sustainable Energy Reviews, 2018, vol. 90, pp. 292-315.

Pinheiro Pires et al., "Challenges and Opportunities for Bio-oil Refining: A Review", Energy & Fuels, 2019, vol. 33, No. 6, pp. 4683-4720.

Rasrendra et al., "Recovery of acetic acid from an aqueous pyrolysis oil phase by reactive extraction using tri-n-octylamine", Chemical Engineering Journal, 2011, vols. 176-177, pp. 244-252.

Ren et al., "Separation of chemical groups from bio-oil water-extract via sequential organic solvent extraction", Journal of Analytical and Applied Pyrolysis, 2017, vol. 123, pp. 30-39.

Winsor, "Hydrotropy, solubilisation and related emulsification processes", Transactions of the Faraday Society, 1948, vol. 44, pp. 376-398.

Zacher et al., "Technology advancements in hydroprocessing of bio-oils", Biomass & Bioenery, 2019, vol. 125, pp. 151-168.

Zhang et al., "Chapter 15—Hydrothermal Carbonization for Hydrochar Production and Its Application", in Biochar from Biomass and Waste, Elsevier, 2019, pp. 275-294.

* cited by examiner

Scheme 1

Scheme 2

RENEWABLE CO-SOLVENTS FOR THERMOCHEMICAL BIO-OIL PROCESSING

CROSS-REFERENCE TO RELATED APPLICATION

This application is a national stage entry from International Patent Application No. PCT/US22/38475 filed on Jul. 27, 2022, which claims priority from U.S. Provisional Patent Application No. 63/227,564 filed on Jul. 30, 2021, which are incorporated by reference herein in the entirety.

STATEMENT OF GOVERNMENT SUPPORT

This invention was made with government support under Contract No. DE-AC36-08GO28308 awarded by the Department of Energy. The government has certain rights in the invention.

TECHNICAL FIELD

This invention relates to systems and methods for preparing renewable co-solvents for thermochemical bio-oil processing.

BACKGROUND

Thermochemical conversion of biomass into bio-oil offers a low-cost route to process diverse biomass feedstocks into condensed oxygenated liquid products for further hydrotreating into liquid transportation fuels. However, there remain needs for improving bio-oil hydrotreating performance, for increasing the chemical stability of both the bio-oil starting materials and the resultant fuels, and for enhancing the overall liquid transportation fuel yield.

SUMMARY

Systems and methods for preparing renewable co-solvents for thermochemical bio-oil processing are described. In particular, systems and methods for preparing oxygenated compounds (e.g., alcohols) from a portion of pyrolysis-derived oil, and for combining the oxygenated compounds with a pyrolysis-derived oil before hydrotreating-thereby recycling the oxgenated compounds—is described. In some embodiments, thermochemical bio-oil includes pyrolysis oil. The pyrolysis oil (or pyrolysis-derived oil) can be prepared from woody biomass. In some embodiments, the co-solvents include one or more alcohols (e.g., one or more C9 alcohols, or a mixture of a C9 alcohol and one or more additional alcohols).

Embodiment 1 is a method of treating pyrolysis oil to yield a liquid fuel or liquid fuel precursor, the method comprising:
  combining the pyrolysis oil with one or more alcohols to yield a mixture; and
  hydrotreating the mixture to yield the liquid fuel or liquid fuel precursor.

Embodiment 2 is the method of embodiment 1, wherein the pyrolysis oil comprises ≤30 wt % water.

Embodiment 3 is the method of embodiment 1 or 2, wherein the pyrolysis oil comprises ≥5 wt % oxygen.

Embodiment 4 is the method any of one of embodiments 1 through 3, wherein the mixture comprises 5 wt % to 95 wt %, 5 wt % to 15 wt %, or 80 wt % to 95 wt % of the one or more alcohols.

Embodiment 5 is the method of embodiment 4, wherein the one or more alcohols comprise one or more C9 alcohols.

Embodiment 6 is the method of embodiment 5, wherein the one or more C9 alcohols comprise a trimethylcyclohexanol.

Embodiment 7 is the method of embodiment 6, wherein the trimethylcyclohexanol comprises 3,3,5-trimethylcyclohexanol.

Embodiment 8 is the method of any one of embodiments 5 through 7, wherein the one or more alcohols further comprise one or more C3 alcohols.

Embodiment 9 is the method of any one of embodiments 1 through 8, wherein the liquid fuel or liquid fuel precursor comprises one or more of methanol, ethanol, isopropyl alcohol, 3,3,5-trimethylcyclohexanol, 1,3,5-trimethylcyclohexane, 1,3,5-trimethylbenzene, 4-heptanol, 6-undecanol, methoxycyclohexane, phenol, 4-propyl-1-cyclohexanol, 1-butanol, 1-octadecanol, and octadecane.

Embodiment 10 is the method of any one of embodiments 1 through 9, wherein the pyrolysis oil has a net heat of combustion of ≥15 MJ/kg.

Embodiment 11 is the method of any one of embodiments 1 through 10, further comprising processing acetic acid to yield the one or more alcohols.

Embodiment 12 is the method of embodiment 11, wherein processing the acetic acid comprises:
  condensing the acetic acid to yield isopropanone;
  oligomerizing the isopropanone to yield isophorone; and
  hydrogenating the isophorone to yield 3,3,5-trimethylcyclohexanol.

Embodiment 13 is the method of embodiment 12, wherein processing the acetic acid further comprises hydrogenating the isopropanone to yield isopropanol.

Embodiment 14 is the method of embodiment 12 or 13, wherein processing the acetic acid further comprises oligomerizing the isopropanone to yield 1,3,5-trimethylbenzene.

Embodiment 15 is the method of embodiment 14, wherein processing the acetic acid further comprises hydrogenating the 1,3,5-trimethylbenzene to yield 1,3,5-trimethylcyclohexane.

Embodiment 16 is the method of any one of embodiments 1 through 15, further comprising separating an aqueous component from the pyrolysis oil before combining the pyrolysis oil with the one or more alcohols.

Embodiment 17 is the method of embodiment 16, wherein the aqueous component comprises the acetic acid, and combining the pyrolysis oil with the one or more alcohols comprises recycling the acetic acid.

Embodiment 18 is the method of any one of embodiments 1 through 17, wherein the pyrolysis oil is derived from woody biomass.

Embodiment 19 is the method of any one of embodiments 1 through 18, wherein the mixture is a single phase mixture.

Embodiment 20 is a liquid fuel or liquid fuel precursor comprising 3,3,5-trimethylcyclohexanol.

Embodiment 21 is the liquid fuel or liquid fuel precursor of embodiment 20, wherein the liquid fuel or liquid fuel precursor is derived from pyrolysis oil.

Advantages of systems and methods described herein include decreasing a viscosity of the pyrolysis oil by the addition of a co-solvent (e.g., one or more oxygen-containing organic compounds, such as one or more alcohols), thereby improving the processing of the pyrolysis oil in the hydrotreating process and incorporating the co-solvent into the liquid fuel and or liquid fuel precursor. Additional advantages include the use (e.g., recycling) of thermochemical aqueous phase components in pyrolysis oil.

The details of one or more embodiments of the subject matter of this disclosure are set forth in the accompanying drawings and the description. Other features, aspects, and advantages of the subject matter will become apparent from the description, the drawings, and the claims.

BRIEF DESCRIPTION OF DRAWINGS

Some embodiments are illustrated in referenced figures of the drawings. It is intended that the embodiments and figures disclosed herein are to be considered illustrative rather than limiting.

DETAILED DESCRIPTION

Figure 1:
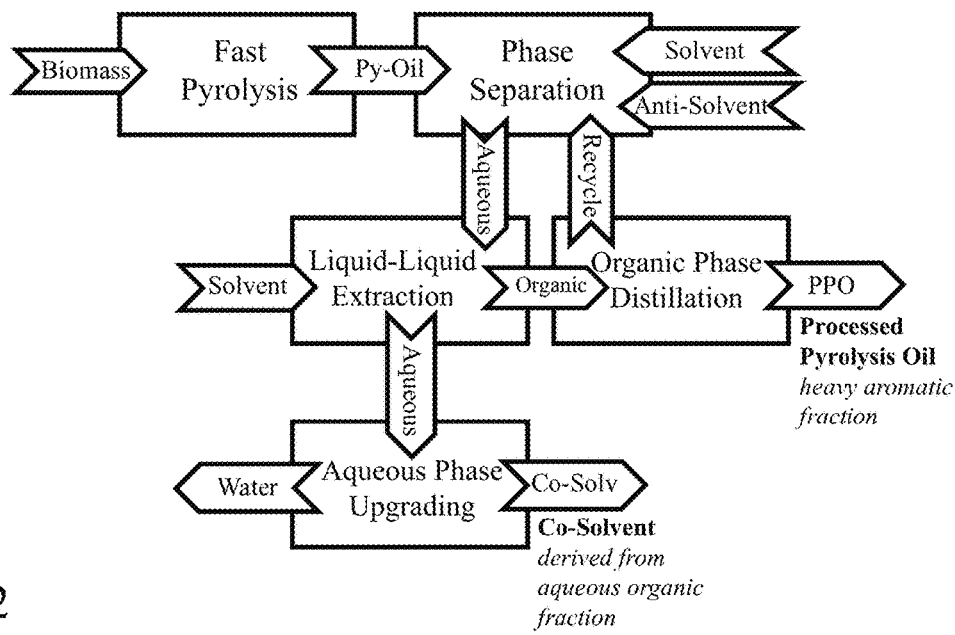
FIG. 1 shows process schematics for co-solvent production pathways that upgrade organics from the aqueous phase (Scheme 1), recycle partially hydrotreated processed pyrolysis oil (Scheme 2), or various combinations thereof, according to some embodiments of the present disclosure.
Figure 1:
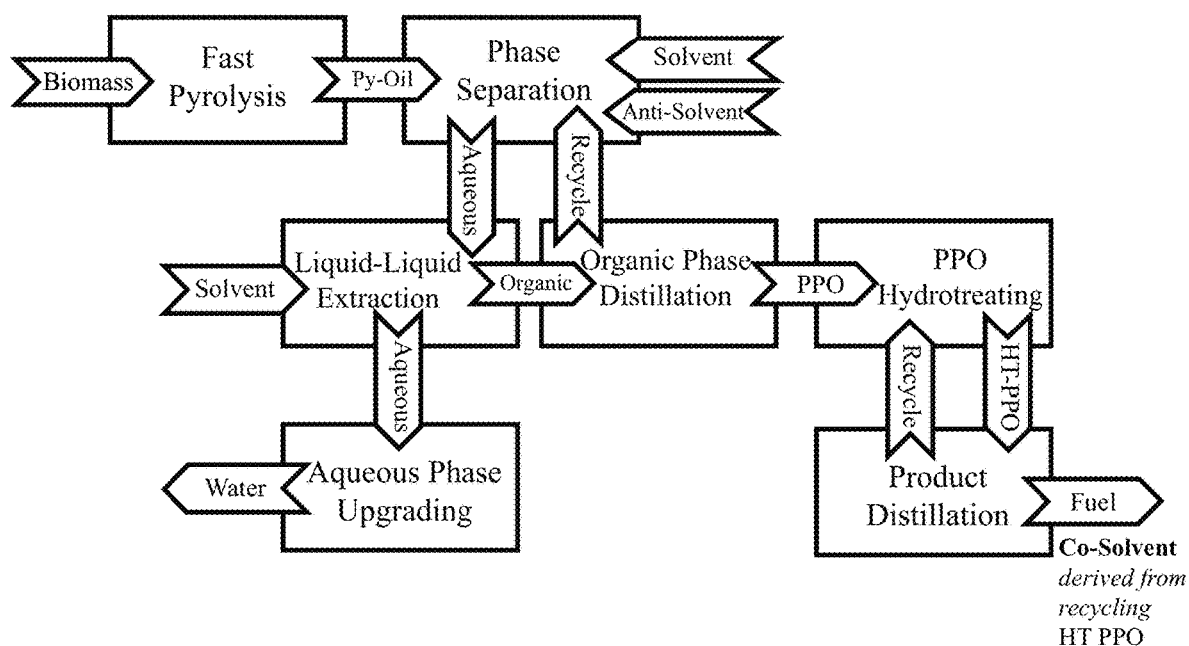

The embodiments described herein should not necessarily be construed as limited to addressing any of the particular problems or deficiencies discussed herein. References in the specification to "one embodiment", "an embodiment", "an example embodiment", "some embodiments", etc., indicate that the embodiment described may include a particular feature, structure, or characteristic, but every embodiment may not necessarily include the particular feature, structure, or characteristic. Moreover, such phrases are not necessarily referring to the same embodiment. Further, when a particular feature, structure, or characteristic is described in connection with an embodiment, it is submitted that it is within the knowledge of one skilled in the art to affect such feature, structure, or characteristic in connection with other embodiments whether or not explicitly described.

As used herein the term "substantially" is used to indicate that exact values are not necessarily attainable. By way of example, one of ordinary skill in the art will understand that in some chemical reactions 100% conversion of a reactant is possible, yet unlikely. Most of a reactant may be converted to a product and conversion of the reactant may asymptotically approach 100% conversion. So, although from a practical perspective 100% of the reactant is converted, from a technical perspective, a small and sometimes difficult to define amount remains. For this example of a chemical reactant, that amount may be relatively easily defined by the detection limits of the instrument used to test for it. However, in many cases, this amount may not be easily defined, hence the use of the term "substantially". In some embodiments of the present invention, the term "substantially" is defined as approaching a specific numeric value or target to within 20%, 15%, 10%, 5%, or within 1% of the value or target. In further embodiments of the present invention, the term "substantially" is defined as approaching a specific numeric value or target to within 1%, 0.9%, 0.8%, 0.7%, 0.6%, 0.5%, 0.4%, 0.3%, 0.2%, or 0.1% of the value or target.

As used herein, the term "about" is used to indicate that exact values are not necessarily attainable. Therefore, the term "about" is used to indicate this uncertainty limit. In some embodiments of the present invention, the term "about" is used to indicate an uncertainty limit of less than or equal to ±20%, ±15%, ±10%, ±5%, or ±1% of a specific numeric value or target. In some embodiments of the present invention, the term "about" is used to indicate an uncertainty limit of less than or equal to ±1%, ±0.9%, ±0.8%, ±0.7%, ±0.6%, ±0.5%, ±0.4%, ±0.3%, ±0.2%, or ±0.1% of a specific numeric value or target.

The present disclosure relates to, among other things, methods that increase the distillate fuel yields obtained from hydrotreating pyrolysis-derived oils (also referred to herein as bio-oil or pyrolysis oil), and compositions obtained therefrom. This is achieved by decreasing the viscosity of the bio-oil by the addition of a co-solvent, which not only improves the processing of the bio-oil in the hydrotreating process, but is also incorporated into the liquid fuel and or liquid fuel precursors. As used herein, "fuel" or "liquid fuel" generally includes liquid transportation fuels, such as gasoline, jet fuel, diesel fuel, and marine fuel. Sustainable aviation fuel (SAF) is one example of a liquid fuel. As used herein, a "fuel precursor" or "liquid fuel precursor" generally refers to a composition that does not meet the defined physico-chemical specifications (e.g., energy density, freeze point, flash point, viscosity, boiling point, etc.) of a given liquid fuel type due at least in part to the excess presence of heteroatoms (e.g., oxygen, nitrogen, sulfur), compounds with olefin bonds, compounds with high molecular weight, compounds with high melting point, or combinations thereof, such that hydrotreating the composition results in a liquid fuel that meets the defined physico-chemical specifications. This in turn, can increase the yield of renewable hydrogen production by oxygenating the co-solvents. Importantly, the co-solvents, e.g., 3,5,5-trimethyl-2-cyclohexen-1-one (i.e., isophorone), may be derived from the short chain acids present in the aqueous phase of biomass thermochemical processes, as well as from fermentation processes.

In some embodiments of the present disclosure, a method for improving the processability of a bio-oil (e.g., pyrolysis-derived oil or pyrolysis oil) may include combining the pyrolysis-derived oil with a molecule (i.e., co-solvent) to form a mixture that is substantially one liquid phase and then hydrotreating the mixture resulting in the synthesis of at least one of a liquid fuel and/or liquid fuel precursor. In some embodiments of the present disclosure, the co-solvent may include at least one of an alcohol, an ester, a ketone, and/or an enone, where the co-solvent may itself be derived from a pyrolysis process and/or fermentation process. Examples of a co-solvent include at least one of methanol, ethanol, 2-propanone, isopropanol, 3,5,5-trimethyl-2-cyclohexen-1-one (i.e., isophorone), 4-heptanone, 4-heptanol, 6-undecanone, 6-undecanol, trimethylcyclohexanol, methoxybenzene, or 4-propyl-1-benzene, 4-propyl-cylohexanol, naphtanlen-2-ol, decahydronaphthalen-2-ol, butyl acetate, 1-butanol, and/or a triglyceride. In general, a fat, an oil, and/or a grease may be utilized and/or synthesized to be utilized as a co-solvent in one or more of the methods and/or systems described herein.

In some embodiments of the present disclosure, the methods may involve the emulsion behavior of fast pyrolysis oil by using a hydrophobic organic solvent and water as a solvent/anti-solvent process. When water and hydrophobic organic solvent are added sequentially to pyrolysis oil, the solvent expels water and small oxygenates from the heavy aromatic fraction to produce a near water-free solvated pyrolytic lignin and solvent that is less dense than the aqueous phase comprised of water, pyrolytic sugars, and small oxygenates. Unlike conventional solvent extraction processes, which depend on the solubility of lignin in the solvent, emulsion-based processes may require much smaller quantities of liquid. The solvent/anti-solvent process may use as little as 10 wt % of hydrophobic solvent/water addition relative to the pyrolysis oil feed.

In some embodiments of the present disclosure, a starting bio-oil, before the addition of a co-solvent, may be characterized by a liquid mixture and/or gas phase mixture that includes at least one of a phenolic, phenol, methoxyphenol, naphtanlen-2-ol, acetic acid, levoglucosan, and/or butyl acetate. Such a mixture may be further characterized by having at least one of a net heat of combustion of greater than about 15 MJ/kg, a water content of less than about 30 wt % and/or an oxygen content greater than about 5 wt %. In some embodiments of the present disclosure, a mixture resulting from the combining of a bio-oil with a co-solvent may be characterized by a composition that includes at one of methanol, ethanol, 2-propanone, isopropanol, isophorone, trimethylcyclohexanol, 4-heptanone, 4-heptanol, 6-undecanone, 6-undecanol, methoxybenzene, 4-propyl-1-benzene, 4-propyl-cylohexanol, naphtanlen-2-ol, decahydronaphthalen-2-ol, isopropyl alcohol, 3,3,5-trimethylcyclohexanol, 1,3,5-trimethylcyclohexane, 1,3,5-trimethylbenzene, methoxycyclohexane, phenol, 4-propyl-1-cyclohexanol, a phenolic, phenol, methoxyphenol, naphtanlen-2-ol, acetic acid, levoglucosan, butyl acetate, 1-butanol, and/or triglyceride.

In some embodiments of the present disclosure, the liquid fuel and/or liquid fuel precursor resulting from the hydrotreating of a bio-oil/co-solvent mixture may be characterized by a composition that includes at least one of methanol, ethanol, butanol, isopropyl alcohol, 3,3,5-trimethylcyclohexanol, 1,3,5-trimethylcyclohexane, 1,3,5-trimethylbenzene, 4-heptanol, 6-undecanol, methoxycyclohexane, phenol, 4-propyl-1-cyclohexanol, 1-octadecanol, and/or octadecane. In the case of ethanol and/or butanol, these molecules may form in the hydrotreating process if butyl acetate is included in the mixture of co-solvent and bio-oil. In the case of 1-octadeconal and/or octodecane, these molecules may form in the hydrotreating process if a triglyceride was present in the mixture of co-solvent and bio-oil.

Other oxygenated (oxygen-containing) co-solvents derived from short chain acids for bio-oil hydrotreating include acetone, butanone, pentanone, heptanone, their enone coupling products, their ester and alcohol derivatives, and mixtures thereof with or without isophorone. As used herein, "short chain acids" refer to organic acids having six carbons or less. Examples of bio-oils include pyrolysis oils (e.g., fast, slow, and/or catalytic pyrolysis), hydrothermal liquefaction oils, and fractionated products from the above bio-oils (e.g., solvent fractioned products from a bio-oil). In some embodiments of the present disclosure, an oxygenated co-solvent as described herein may include a C8 molecule that includes at least one of an oxygenated ketone, an enone, an ester, and/or an alcohol derived from at least one short chain acid that is soluble with the bio-oil upon mild heating. In some embodiments of the present disclosure, an oxygenated co-solvent as described herein may be a molecule having eight or more carbon atoms that includes at least one of an oxygenated ketone, an enone, an ester, and/or an alcohol derived from at least one short chain acid that is soluble with the bio-oil upon mild heating.

Among other things, utilization of the co-solvents in bio-oils may reduce viscosity limitations that are typically present during the thermochemical processing of bio-oils, for example, during hydrotreating, as well as enabling the utilization of thermochemical aqueous phase carbon. During hydrotreating, a co-solvent may enable the generation of transportation range hydrocarbon fuels, which in turn, increases overall process yields and improves process economics. In addition, light gases (e.g., $H_2O$, CO, $CO_2$) and low molecular weight organic molecules (e.g., alcohols, aldehydes, ketones, and organic acids) produced from hydrotreating the co-solvent may be further processed to generate renewable hydrogen resulting in, among other things, a lower overall carbon footprint for producing the fuel.

Further, in some embodiments of the present disclosure, co-solvents having a carbon chain length of five or more carbon atoms may be used to generate liquid hydrocarbons during hydrotreating, which can improve the overall fuel process yield and economics. For co-solvents having carbon chain lengths less than or equal to four carbon atoms, light hydrocarbon gases may be generated during hydrotreating, which can be subsequently processes via a steam reforming step to generate renewable hydrogen and lower the lifecycle carbon footprint of the process.

Among other things, routes are described herein for generating co-solvents from thermochemical processing as illustrated in FIG. 1. Scheme 1 shows a process schematic for co-solvent production pathways that upgrade organics from the aqueous phase. Scheme 2 shows a process schematic for recycling of partially hydrotreated processed pyrolysis oil. These routes include converting aqueous phase organics into acetic acid, which may be further upgraded catalytically into oxygenate-rich co-solvents through coupling and hydrogenation reactions, as shown in Reactions 1-3, and partially deoxygenating bio-oil itself during hydrotreating, followed by recycle, as shown in Reactions 4-5 with representative bio-oil compounds.

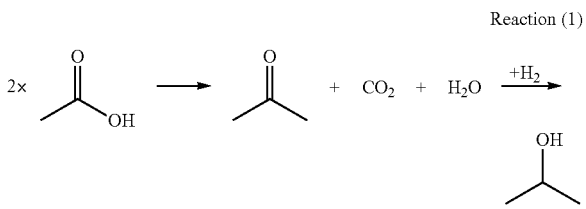

Reaction (1)

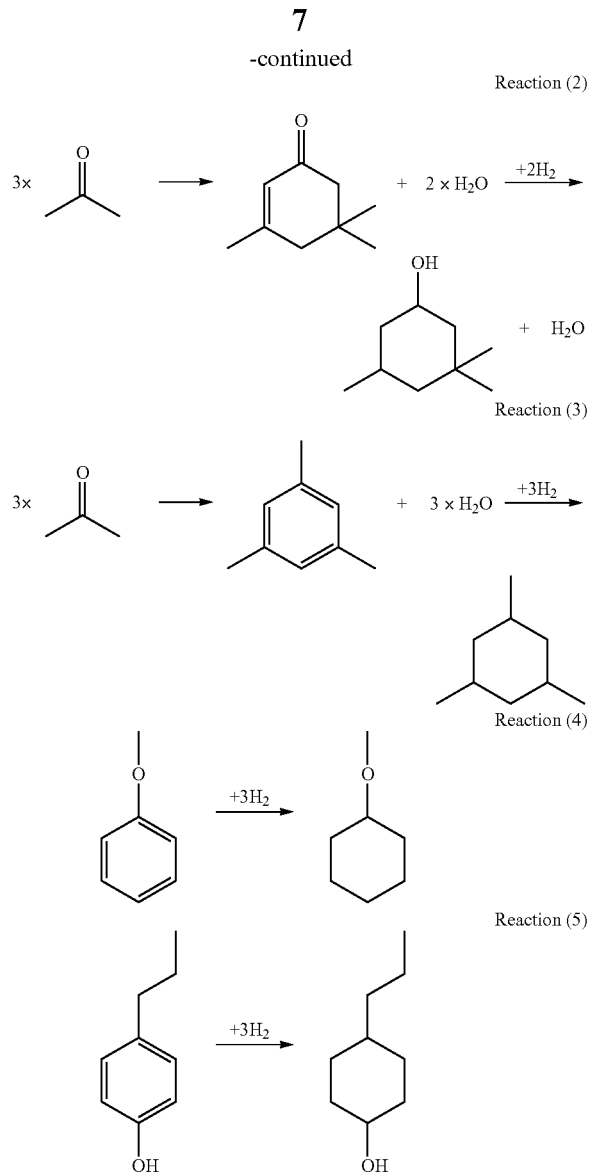

Reaction (2)

Reaction (3)

Reaction (4)

Reaction (5)

Referring to Reactions 1-5 above, Reaction (1) illustrates the reaction of acetic acid to produce 2-propanone (and $CO_2$ and water), which may then be hydrogenated (e.g., in a hydrotreater) to produce isopropyl alcohol (IPA). Reaction (2) illustrates the conversion of 2-propanone to isophorone (and water), followed by the hydrogenation of isophorone to produce 3,3,5-trimethylcyclohexanol (TMCH—OH). Reaction (3) illustrates the conversion of 2-propanone to 1,3,5-trimethylbenzene, followed by the hydrogenation of 1,3,5-trimethylbenzene to produce 1,3,5-trimethylcyclohexane (TMCH—HC). Reaction (4) illustrates the hydrogenation reaction of methoxybenzene to produce methoxycyclohexane. Reaction (5) illustrates the hydrogenation reaction of 4-propyl-1-benzene to produce 4-propyl-1-cyclohexanol.

Referring again to Reactions 1-5, the unsaturated molecules provide examples of co-solvents, according to some embodiments of the present disclosure. Thus, specific examples of co-solvents include 2-propanone, isophorone, 1,3,5-trimethylbenzene, methoxybenzene, and 4-propyl-1-benzene. Therefore, once these molecules are processed along with the bio-oil in a hydrotreater, and/or reacted with hydrogen alone in a separate reaction step, at least a portion of one or more of these co-solvents may be converted to at least one of IPA, 3,3,5-trimethylcyclohexanol, 1,3,5-trimethylcyclohexane, methoxycyclohexane, and/or 4-propyl-1-cyclohexanol, respectively. These hydrogenated molecules may then be present in the resultant fuels where, among other things, they increase the oxygen content of the fuel. They can also serve as "markers" indicating the use of the co-solvents in the upstream processing steps described herein.

In some embodiments, treating pyrolysis oil to yield a liquid fuel or liquid fuel precursor includes combining the pyrolysis oil with a co-solvent as described in any embodiment herein to yield a mixture, and hydrotreating the mixture as described in any embodiment herein to yield the liquid fuel or liquid fuel precursor. The mixture can be a single liquid phase as described herein. The co-solvent can include, consist of, or consist essentially of one or more alcohols. The pyrolysis oil can be derived from woody biomass, for example, as described herein. In some cases, the pyrolysis oil includes ≤30 wt % water, ≥5 wt % oxygen, or both, as described herein. The pyrolysis oil typically has a net heat of combustion of ≥15 MJ/kg. The one or more alcohols can include a mixture of two or more alcohols. The co-solvent can be pyrolysis-derived or fermentation-derived. The liquid fuel can be a transportation fuel, such as gasoline, diesel fuel, jet fuel, or marine fuel. The liquid fuel precursor can be a transportation fuel precursor, such as gasoline precursor, diesel fuel precursor, jet fuel precursor, or marine fuel precursor.

The mixture can include 5 wt % to 95 wt % of the one or more alcohols. In one example, the mixture includes 5 wt % to 15 wt % of the one or more alcohols. In another example, the mixture includes 80 wt % to 95 wt % of the one or more alcohols. In other examples, the mixture includes less than 50 wt % or more than 50 wt % of the one or more alcohols.

The one or more alcohols can include one or more C9 alcohols. The C9 alcohol can be a trimethylcyclohexanol, such as 3,3,5-trimethylcyclohexanol. In some cases, the one or more alcohols include one or more C9 alcohols and one or more C3 alcohols, as described herein. In certain cases, the liquid fuel or liquid fuel precursor includes one or more of methanol, ethanol, isopropyl alcohol, 3,3,5-trimethylcyclohexanol, 1,3,5-trimethylcyclohexane, 1,3,5-trimethylbenzene, 4-heptanol, 6-undecanol, methoxycyclohexane, phenol, 4-propyl-1-cyclohexanol, 1-butanol, 1-octadecanol, and octadecane.

Some embodiments include processing acetic acid to yield the one or more alcohols, as described herein, for example, with respect to Reactions 1-5. In one example, as described herein, processing the acetic acid includes condensing the acetic acid to yield isopropanone, oligomerizing the isopropanone to yield isophorone, and hydrogenating the isophorone to yield 3,3,5-trimethylcyclohexanol. In some cases, as described herein, processing the acetic acid can further include hydrogenating the isopropanone to yield isopropanol. In certain cases, as described herein, processing the acetic acid can further include oligomerizing the isopropanone to yield 1,3,5-trimethylbenzene, and optionally hydrogenating the 1,3,5-trimethylbenzene to yield 1,3,5-trimethylcyclohexane.

As described herein, some embodiments include separating an aqueous component from the pyrolysis oil before combining the pyrolysis oil with the one or more alcohols. The aqueous component can include the acetic acid, and combining the pyrolysis oil with the one or more alcohols can include recycling the acetic acid, as described herein.

A liquid fuel or liquid fuel precursor prepared as described herein can include 3,3,5-trimethylcyclohexanol. The liquid or liquid fuel precursor can be bioderived.

In some embodiments, treating pyrolysis oil to yield a liquid fuel or liquid fuel precursor includes combining a pyrolysis-derived oil (a pyrolysis oil) with a molecule to form a mixture that is substantially one liquid phase, and hydrotreating the mixture, resulting in at least one of a liquid fuel or liquid fuel precursor. The molecule can include at least one of an alcohol, an ester, a ketone, or an enone. The molecule can be pyrolysis-derived or fermentation derived.

In some examples, the molecule includes at least one of methanol, ethanol, 2-propanone, isopropanol, 3,5,5-trimethyl-2-cyclohexen-1-one (i.e., isophorone), trimethylcyclohexanol, 4-heptanone, 4-heptanol, 6-undecanone, 6-undecanol, methoxybenzene, or 4-propyl-1-benzene, 4-propylcylohexanol, naphtanlen-2-ol, decahydronaphthalen-2-ol, butyl acetate, 1-butanol, and triglyceride. The liquid fuel or liquid fuel precursor can include at least one of methanol, ethanol, isopropyl alcohol, 3,3,5-trimethylcyclohexanol, 1,3,5-trimethylcyclohexane, 1,3,5-trimethylbenzene, 4-heptanol, 6-undecanol, methoxycyclohexane, phenol, 4-propyl-1-cyclohexanol, 1-butanol, 1-octadecanol, and octadecane. The pyrolysis-derived oil can include one or more of a phenolic, a phenol (e.g., a methoxyphenol), naphtanlen-2-ol, acetic acid, levoglucosan, and butyl acetate. A net heat of combustion of the pyrolysis-derived oil can be >15 MJ/kg. A water content of pyrolysis-derived oil can be <30 wt %. An oxygen content of the pyrolysis-derived oil can be >5 wt %.

In some examples, the mixture includes at least one of methanol, ethanol, 2-propanone, isopropanol, 3,5,5-trimethyl-2-cyclohexen-1-one (i.e., isophorone), trimethylcyclohexanol, methoxybenzene, or 4-propyl-1-benzene, 4-propylcylohexanol, naphtanlen-2-ol, decahydronaphthalen-2-ol, 4-heptanone, 4-heptanol, 6-undecanone, 6-undecanol, methoxycyclohexane, phenol, 4-propyl-1-cyclohexanol, a phenolic, phenol, methoxyphenol, naphtanlen-2-ol, acetic acid, levoglucosan, butyl acetate, 1-butanol, and triglyceride.

EXAMPLES

To demonstrate the ability of oxygenated co-solvents to improve bio-oil viscosity and hydrotreating performance, experiments were performed using an exemplary pyrolysis oil prepared as described with respect to FIGS. 2-6, referred to herein as processed pyrolysis oil (PPO), which was derived from commercially available woody biomass fast pyrolysis oil. Initial tests were performed to examine the viscosity and thermal stability impacts of both alcohol and ketone co-solvents on PPO, as well demonstrate that acetic acid can be converted into mixed oxygenates with suitable co-solvent properties. Hydrotreating product yields were assessed using PPO and select co-solvent mixtures. It should be noted that although pyrolysis oil as prepared with respect to FIGS. 2-6 was tested, the results of which are described herein, the methods and compositions described herein are applicable to pyrolysis oils prepared by alternative processes.

Figure 2:
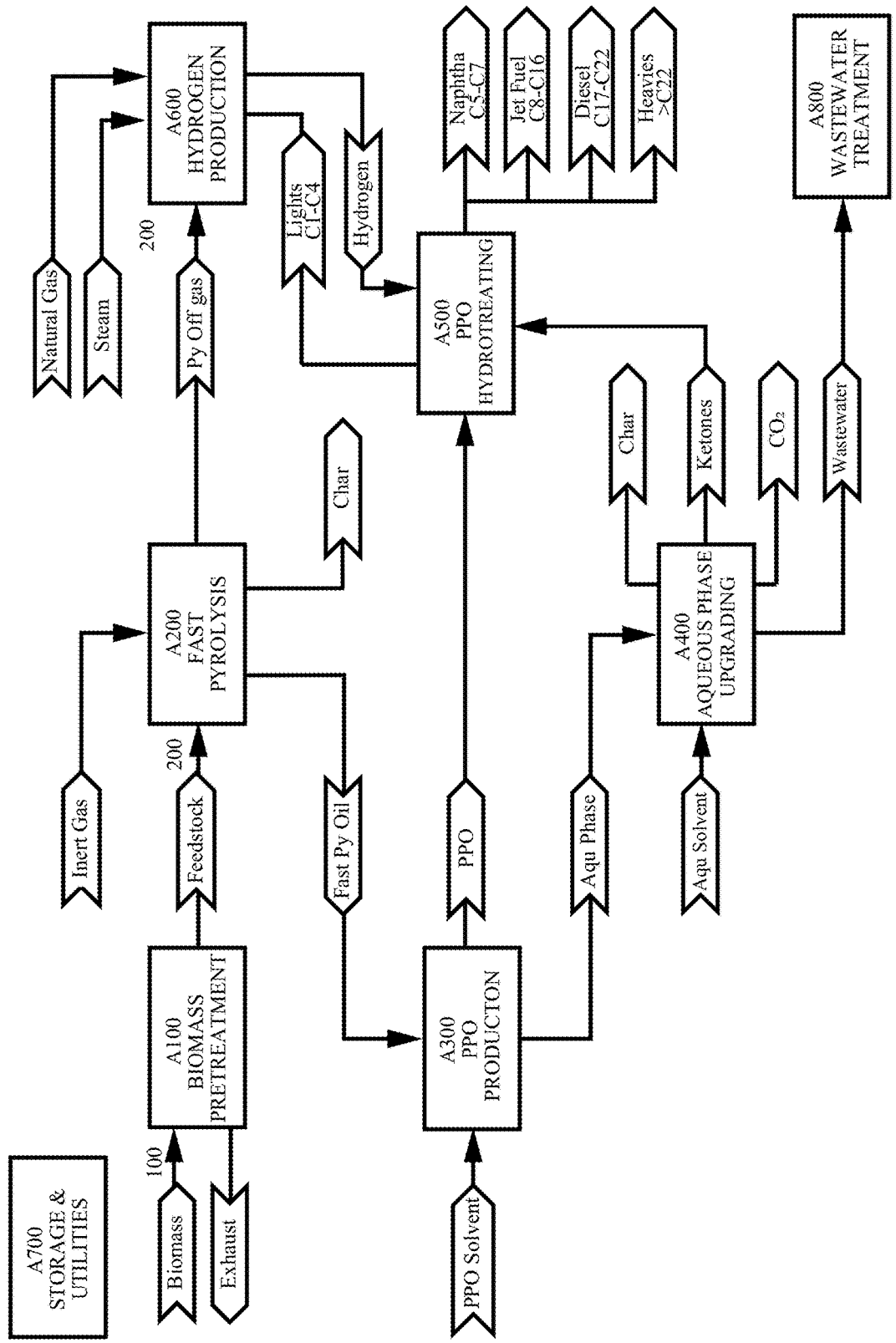
FIG. 2 illustrates a high-level block flow diagram representing a baseline integrated process model for producing liquid fuels from woody biomass.

FIG. 2 is a block flow diagram depicting an example process for producing PPO and liquid fuels/liquid fuel precursors within an integrated biorefinery. FIGS. 3-6 show areas depicted in FIG. 2 in additional detail. The example process includes the following plant areas and unit operations.

Area 100: Biomass Pretreatment. Biomass is initially received and prepared for fast pyrolysis processing. Pretreatment includes grinding and drying steps.

Area 200: Fast Pyrolysis. Biomass is processed by fast pyrolysis using commercial technology to produce bio-oil. The fast pyrolysis unit includes char separation (cyclones), char and process light gas combustion, and bio-oil recovery. The bio-oil product is assumed to be single phase with char and particulate matter removed, meeting the ASTM D7554 commodity boiler fuel specification.

Area 300: PPO Production. Fast pyrolysis oil is split into a hydrophobic heavy aromatic organic phase (PPO) and aqueous phase organics using a solvent fractionation process. PPO is generated by recovering the hydrophobic solvent by distillation to produce an organic phase that contains <1 wt % water and <2 wt % residual solvent with 2× the higher heating value (HHV) of fast pyrolysis oil feed. Aqueous phase organics are sent to Area 400 for concentrating into boiler fuel for the baseline model. PPO is sent to Area 500 for hydrotreating into liquid fuel.

Area 400: Aqueous Phase Upgrading. The aqueous phase can be concentrated for use as residual boiler fuel for on-site energy combustion. This unit operation can be adapted to evaluate aqueous phase organic upgrading to increase liquid fuel yields via catalytic processing of short chain acids. In one example, aqueous phase organics are initially subjected to a hydrothermal treatment process that converts pyrolytic sugars into predominantly acetic acid and hydrothermal char. Acetic acid can be recovered from the aqueous phase by solvent extraction and distillation. The extracted acids can then be processed over a catalytic ketonization-condensation reactor to generate an enone/ketone organic process stream, $CO_2$, and water with trace organics for wastewater treatment.

Area 500: PPO Hydrotreating. PPO from Area 300 is sent for hydrotreating on-site within a fully integrated biorefinery configuration, as depicted here. The $1^{st}$-stage hydrotreater reduces the oxygen content to below 3 wt % over commercial sulfided metal oxide catalysts, while retaining 80% of the bio-oil C. The resulting organic phase is then sent to a $2^{nd}$-stage hydrotreater to fully deoxygenate the fuel, crack heavies, and produce liquid fuel that meets ASTM specifications a selected fuel (e.g., SAF).

Area 600: Hydrogen Production. Hydrogen can be generated by steam reforming of process off-gases generated during fast pyrolysis and hydrotreating. Natural gas can be used for make-up to meet the overall hydrogen demand, with process steam produced via heat integration.

Area 700: Storage and Utilities. This area includes plant utilities, such as electric power, cooling water, plant and instrument air, and process water. It can also include storage for intermediates (liquid fuel precursors) and products (liquid fuels).

Area 800: Wastewater Treatment. The wastewater treatment area can be used to treat plant wastewater in an aerobic basin. After treatment, the water can be reused by the process. Wastewater is generated at several points in the process, including the solvent fraction separation step, the upgrading section, and the steam boiler. The wastewater treatment area can be used to remove these organics.

Figure 3:
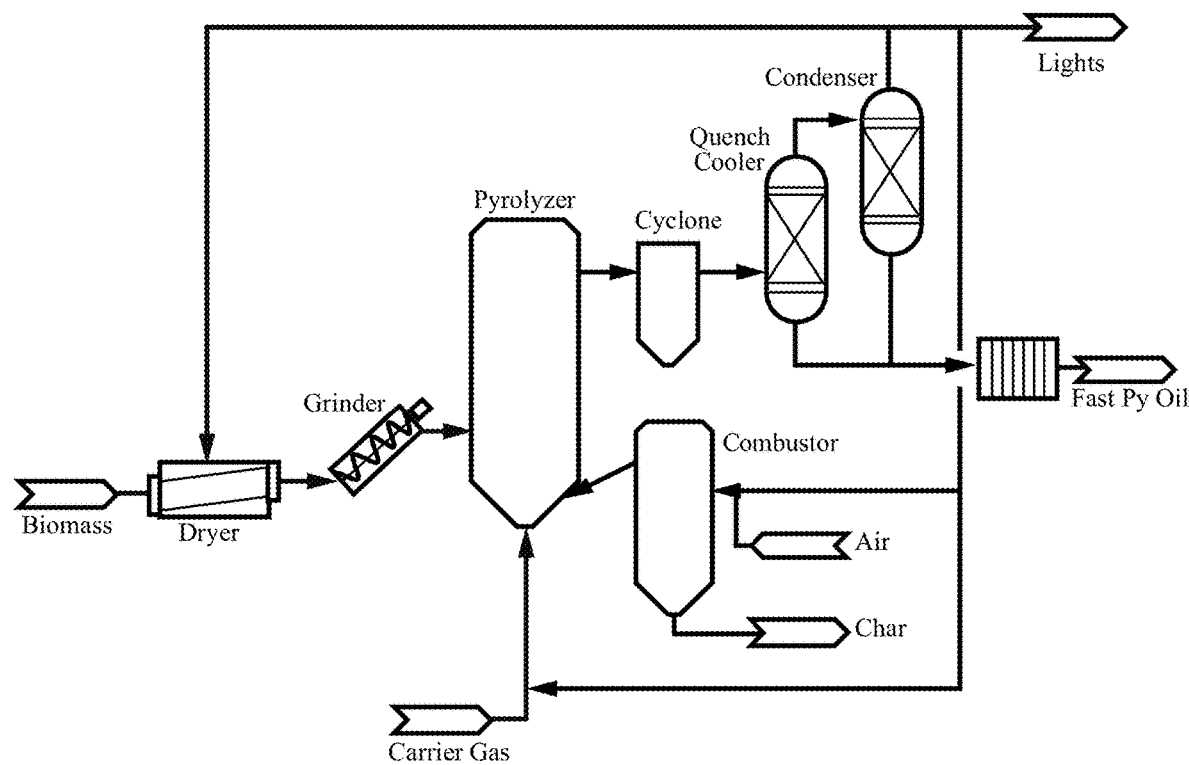
FIG. 3 illustrates a detailed block flow diagram for the fast pyrolysis process, included as Area 200 of FIG. 2.

FIG. 3 illustrates a detailed block flow diagram for a fast pyrolysis process, included as Area 200 of FIG. 2. Biomass can be processed by fast pyrolysis using commercial technology to produce bio-oil. The fast pyrolysis unit includes char separation (cyclones), char and process light gas combustion, and bio-oil recovery.

Figure 4:
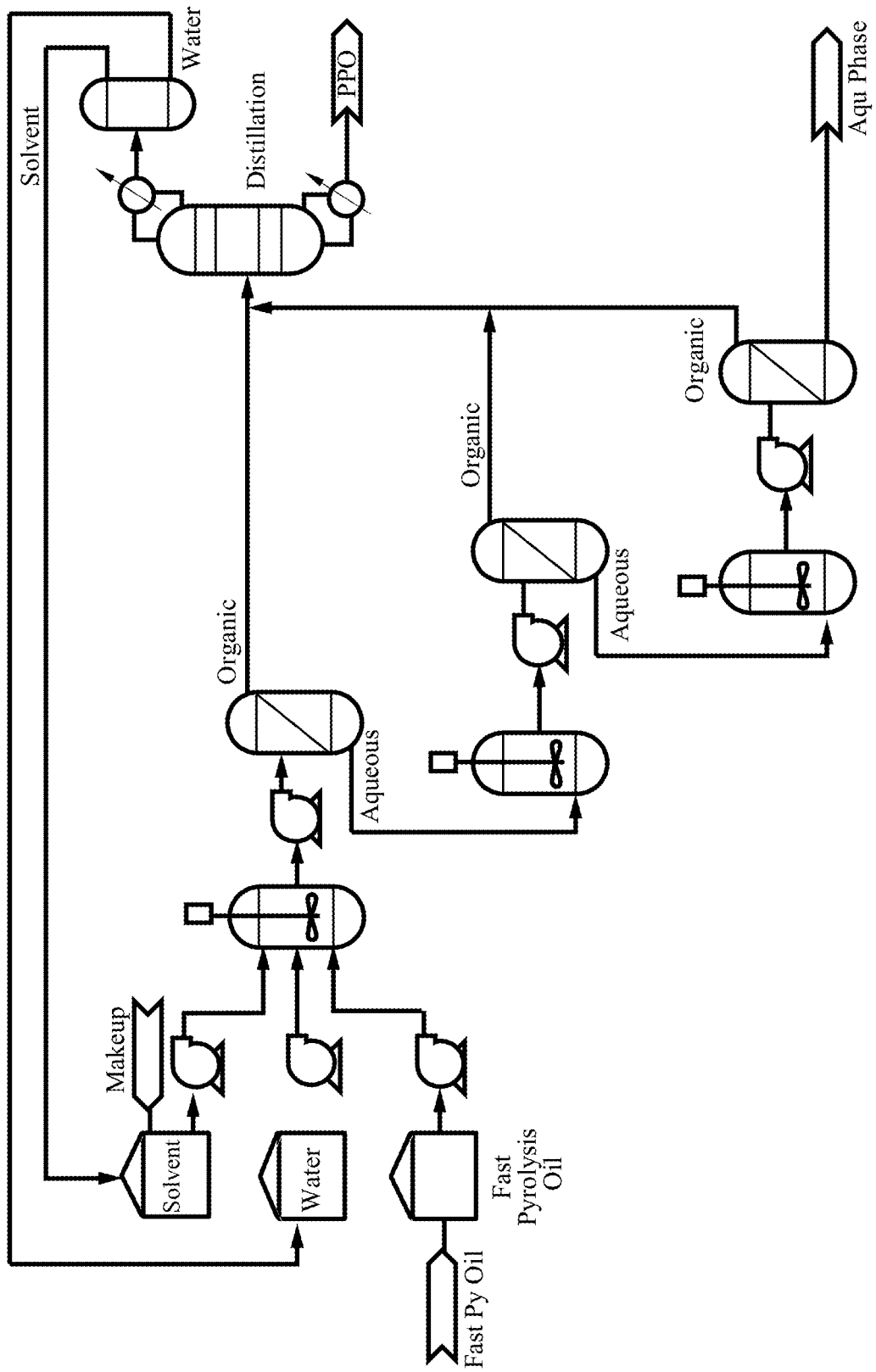
FIG. 4 illustrates a detailed block flow diagram depicting an example production process to yield processed pyrolysis oil (PPO), included as Area 300 of FIG. 2.

FIG. 4 illustrates a detailed block flow diagram depicting an example production process to yield PPO, included as Area 300 of FIG. 2. Fast pyrolysis oil is split into a hydrophobic heavy aromatic organic phase (PPO) and aqueous phase organics using a solvent fractionation process. PPO is generated by recovering the hydrophobic solvent by distillation to produce an organic phase that contains <1 wt % water and <2 wt % residual solvent with 2 times the higher heating value (HHV) of fast pyrolysis oil feed. Aqueous phase organics are sent to Area 400 of FIG. 2 for concentrating into boiler fuel for the baseline model. PPO is sent to Area 500 of FIG. 2 for hydrotreating into liquid fuel.

Figure 5:
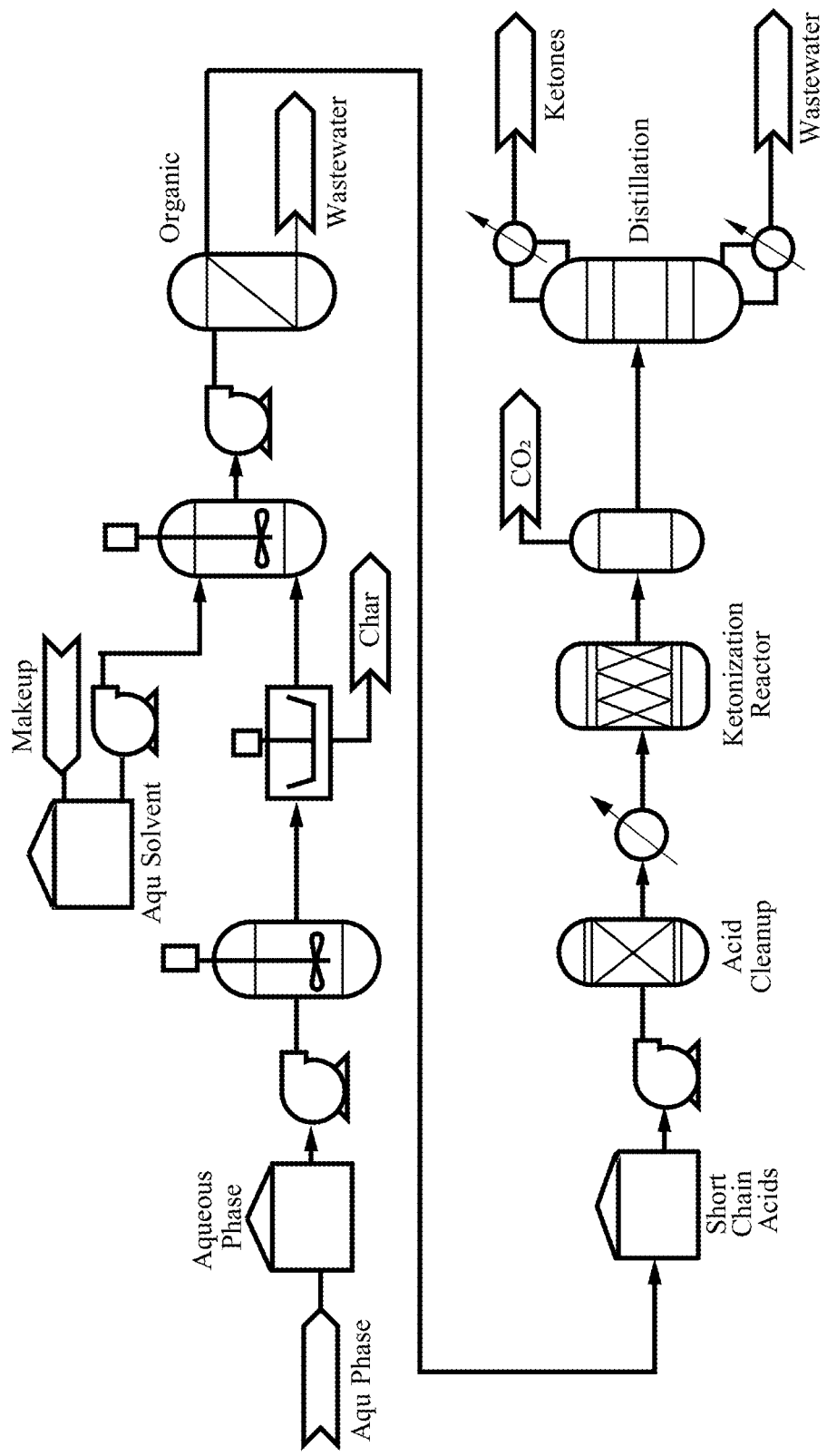
FIG. 5 illustrates a block flow diagram for an example aqueous phase upgrading process, included as area 400 of FIG. 2.

FIG. 5 illustrates a block flow diagram for an example aqueous phase upgrading process, included as area 400 of FIG. 2. The aqueous phase is upgraded to increase liquid fuel yields via catalytic processing of short chain acids as described herein. Acetic acid is recovered from the aqueous phase by solvent extraction and distillation. The extracted acids are then processed over a catalytic ketonization-condensation reactor to generate an enone/ketone organic process stream, $CO_2$, and water with trace organics for wastewater treatment.

Figure 6:
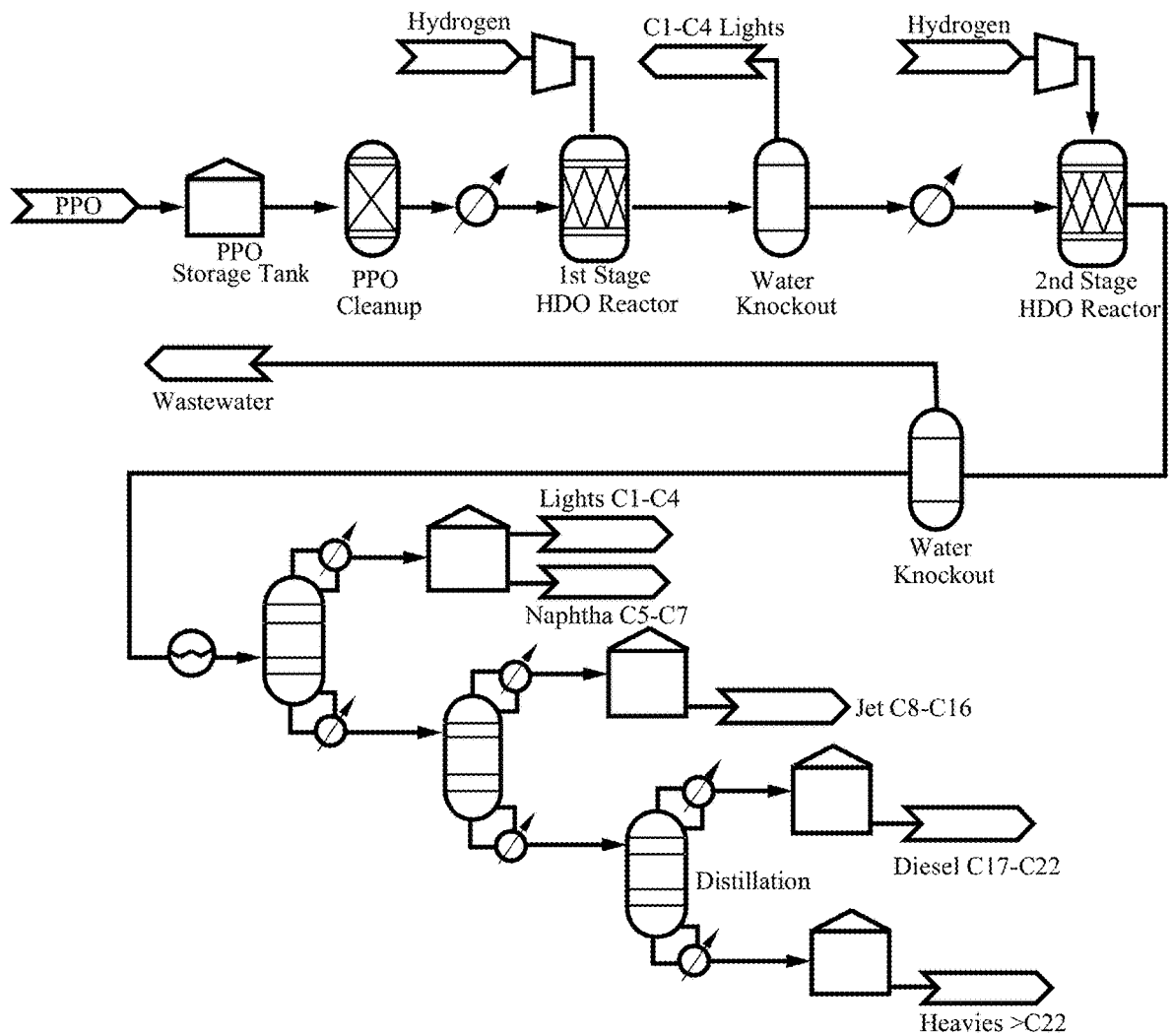
FIG. 6 illustrates a block flow diagram for an example of hydrotreating processed pyrolysis oil, included as Area 500 of FIG. 2.

FIG. 6 illustrates a block flow diagram for an example of hydrotreating processed pyrolysis oil, included as Area 500 of FIG. 2. PPO from Area 300 of FIG. 2 can be sent for hydrotreating on-site within a fully integrated biorefinery configuration. The 1st-stage hydrotreater reduces the oxygen content to below 3 wt % over commercial sulfided metal oxide catalysts, while retaining 80% of the bio-oil carbon. The resulting organic phase is then sent to a 2nd-stage hydrotreater to fully deoxygenate the fuel, crack heavies, and produce liquid fuel.

Experimental

Example 1. Acetic Acid Upgrading to Co-Solvent

Figure 7:
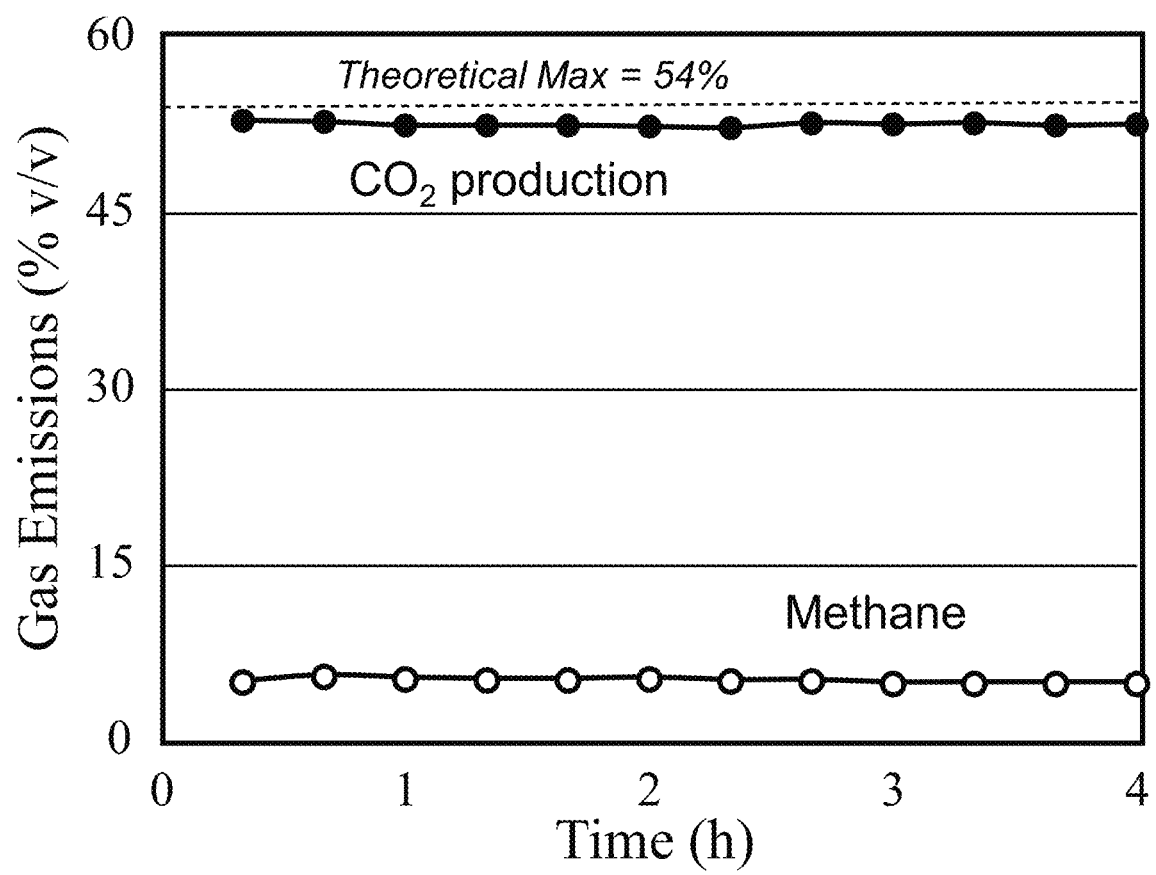
FIG. 7 illustrates gas product yields during the ketonization and condensation of neat acetic acid.

Acetic acid upgrading to co-solvent. Tests confirmed the ability to convert acetic acid into C3 and Co oxygenates, which has relevance due to the prevalence of acetic acid in thermochemical aqueous process streams. FIG. 7 illustrates gas product yields during the ketonization and condensation of neat acetic acid. Reaction conditions were as follows: catalyst loading 3 g of $ZrO_2$, bed temperature 400° C., helium gas flow rate of 35 cm$^3$ (STP) min-1, weight hourly space velocity of 3.6 h$^{-1}$. Complete conversion of acetic acid was observed, with near theoretical yields of $CO_2$ from ketonization (see Reaction 1).

Figure 8:
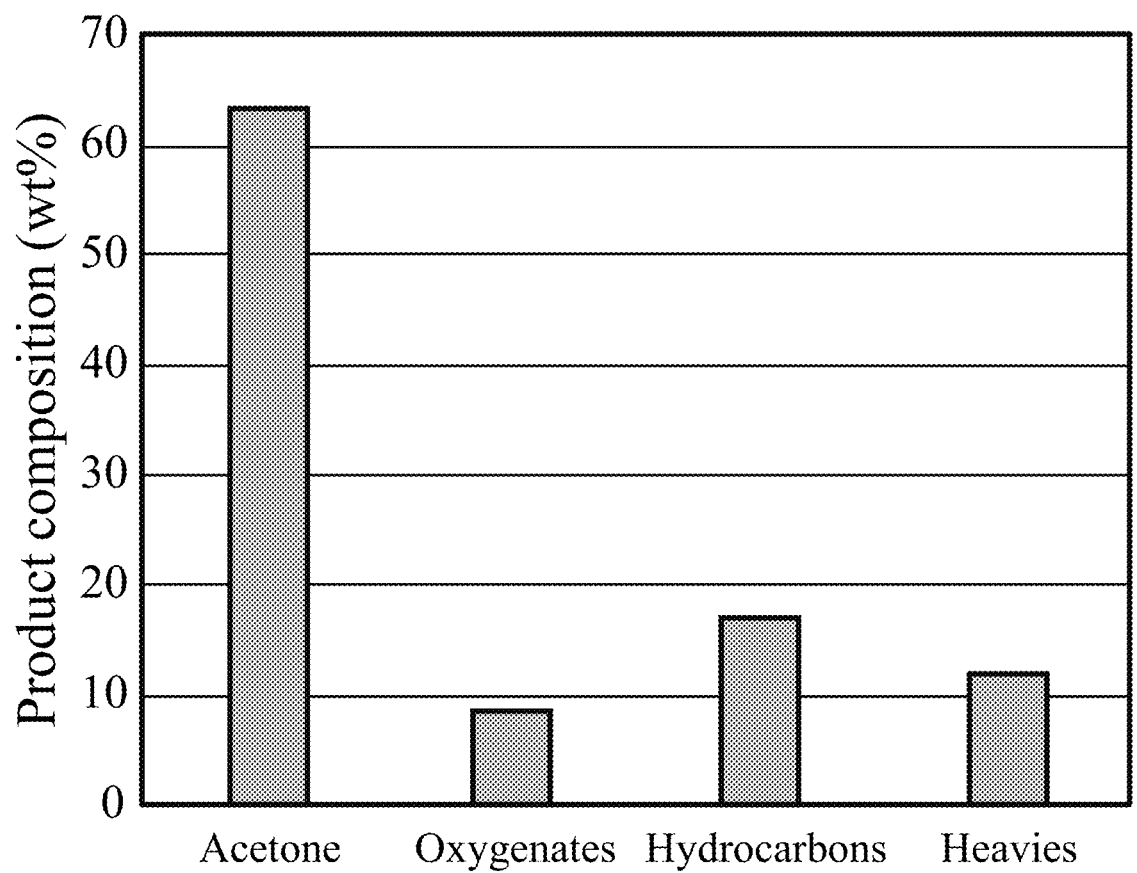
FIG. 8 illustrates organic liquid product yields from the ketonization and condensation of acetic acid, according to the reactions described below, according to some embodiments of the present disclosure.

Methane emissions were steady at 5 vol %, which may be due to mild cracking of the acetic acid feed or resulting ketone and enone products. Liquid mass recovery was 84% of theoretical, from both an organic phase layer and aqueous phase layer. As shown in FIG. 8, the organic phase contained predominantly acetone, as well as C9 oxygenates and hydrocarbons resulting from the aldol condensation of acetone and subsequent dehydration reactions. Later eluting compounds were also observed by GC-MS, herein referred to as "heavy products".

Example 2. Viscosity and Accelerated Aging

Viscosity and accelerated aging. Viscosity and accelerated aging tests were completed to evaluate the ability of co-solvents to improve the flowability of PPO and avoid undesired polymerization side reactions at a temperature of about 100° C. for extended periods of time. The process used to produce PPO typically results in a high-viscosity liquid that makes feeding the PPO into a hydrotreater problematic, as indicated by the measured viscosity of 4183 cP at 40° C. shown in Table 1. The alcohol and ketone co-solvents reduced the viscosity of PPO at various co-solvent loading levels. Accelerated aging tests performed at 100° C. demonstrated the superior thermal stability of alcohol co-solvents relative to ketones. The acetone and isophorone co-solvent displayed a viscosity increase after about 24 hours at about 100° C., while much smaller viscosity changes were observed in both the methanol and IPA/trimethlycyclohexanol (TMCH—OH)/trimethylcyclohexane (TMCH—HC) co-solvents. These viscosity results suggest ketone functional groups may be more reactive as a co-solvent, relative to corresponding alcohols of the same carbon number and carbon chain arrangement (e.g., cyclic, linear, branched).

TABLE 1

Viscosity measurements of BTG fast pyrolysis oil (available from BTG Bioliquids), PPO, and PPO with varying co-solvents (wt %). Viscosity measurements were performed at the temperature indicated, with accelerated aging performed at the time and temperature indicated.

| Sample | Aging at 100° C. | Viscometer Temp (° C.) | Measured Viscosity (cP) |
|---|---|---|---|
| BTG fast pyrolysis oil | None | 40 | 47 |
| Neat PPO | None | 40 | 4183 |
| Neat PPO | None | 50 | 1665 |
| PPO with 20% methanol | None | 40 | 61 |
| PPO with 20% methanol | 24 h | 40 | 122 |
| PPO with 5% 4-heptanone | None | 50 | 870 |
| PPO with 5% 6-undecanone | None | 50 | 1046 |
| PPO with 5% isophorone | None | 50 | 1800 |
| PPO with 10% isophorone | None | 50 | 1577 |
| PPO with 7% acetone, 3% isophorone | None | 50 | 327 |
| PPO with 7% acetone, 3% isophorone | 24 h | 50 | 1040 |
| PPO with 7.5% IPA, 1.25% TMCH-OH, 1.25% TMCH-CH | None | 40 | 359 |
| PPO with 7.5% IPA, 1.25% TMCH-OH, 1.25% TMCH-CH | 24 h | 40 | 479 |
| PPO with 15% IPA, 2.5% TMCH-OH, 2.5% TMCH-CH | None | 40 | 107 |
| PPO with 15% IPA, 2.5% TMCH-OH, 2.5% TMCH-CH | 24 h | 40 | 180 |

Example 3. PPO Hydrotreating

PPO hydrotreating. First stage hydrotreating of PPO in various co-solvents was then performed to track the hydrocarbon liquid oil carbon yield, as well as gas phase carbon yield as a percentage of the PPO feed. For the methanol co-solvent (20 wt %), high carbon balance closure between 97% and 102% was observed for over 100 hours of reactor time-on-stream (see Table 2). A significant portion of the original carbon in the PPO was converted into liquid hydrocarbon oil products, which ranged between 76% and 82%. Direct oxygen analysis confirmed <0.3 wt % of oxygen remained in the organic liquid product, with simulated distillation by gas chromatography indicating over 70% of the sample contained jet fuel range hydrocarbons.

For the methanol/isophorone (9 wt %/9 wt %) co-solvent, lower carbon balance closure was obtained with values of about 91-92% observed in the first two samples (see Table 3), which suggests that carbon deposition may have occurred inside the reactor tube due to polymerization reactions. After shutdown and reactor disassembly, excessive coke and tar formation was observed throughout the catalyst bed that made it problematic to unload, which was not observed with the alcohol co-solvents. Direct oxygen analysis confirmed less than about 0.3 wt % of oxygen remained in the organic liquid product, with GC analysis confirming the isophorone co-solvent resulted in higher trimethlycyclohexane yields when compared to methanol as a co-solvent (see Table 4). In addition, the accelerated aging viscosity test results suggest that ketones are reactive and that hydrogenation to the corresponding alcohol may improve co-solvent stability.

TABLE 2

Carbon balance, as percent of the PPO feed, during hydrotreating with methanol co-solvent.

| Co-Solvent | Time on Stream (h) | Oil Yield (C-yield %) | Gas (C-yield %) | C-Yield Closure |
|---|---|---|---|---|
| Methanol | 29-41 | 82% | 21% | 102% |
| 20 wt % | 41-53 | 80% | 21% | 101% |
|  | 87-99 | 79% | 20% | 99% |
|  | 99-111 | 76% | 21% | 97% |

TABLE 3

Carbon balance, as percent of the PPO feed, during hydrotreating with methanol and isophorone co-solvent.

| Co-Solvent | Time on Stream (h) | Oil Yield (C-yield %) | Gas (C-yield %) | C-Yield Closure |
|---|---|---|---|---|
| Methanol 9 wt % | 23-35 | 74% | 18% | 92% |
| Isophorone 9 wt % | 35-47 | 74% | 16% | 91% |
|  | 47-60 | 83% | 17% | 100% |

TABLE 4

Hydrocarbon products identified by gas chromatography-mass spectroscopy in the hydrotreated product when using PPO co-solvent feed.

| GC-Identified Hydrocarbon | Hydrotreated Product from PPO and 20 wt % MeOH (wt %) | Hydrotreated Product from PPO with 9 wt % Methanol and 9 wt % Isophorone (wt %) |
|---|---|---|
| Cyclohexane | 0.8 | 3.1 |
| Methylcyclohexane | 1.0 | 4.1 |
| Ethylcyclohexane | 0.6 | 2.1 |
| Trimethylcyclohexane | Below detection | 15.0 |

Mixed C3 and C9 alcohols were tested as a co-solvent that could be produced from the mild hydrogenation of acetone and isophorone. The corresponding C9 cyclic hydrocarbon was also included, since it can also be formed during dehydration and hydrogenation reactions (see Reaction 2 and 3). High yield to liquid phase hydrocarbons was observed for 196 h of time-on-stream (see Table 5). After shutdown, no plugging issues were observed during the catalyst bed unloading. These findings, along with the accelerated aging viscosity results, show that C3 and C9 alcohols are suitable co-solvents for PPO hydrotreating.

TABLE 5

Oil mass yield, as percent of the PPO feed, during hydrotreating with isopropanol, trimethylcyclohexanol (TMCH-OH), and trimethylcyclohexane (TMCH-HC) co-solvent.

| Co-Solvent | Time on Stream (h) | Oil Yield (mass yield of feed %) |
|---|---|---|
| IPA 13.5 wt % | 36 | 47 |
| TMCH-OH 2.25 wt % | 66 | 48 |
| TMCH-HC 2.25 wt % | 102 | 49 |
|  | 167 | 47 |

Figure 9:
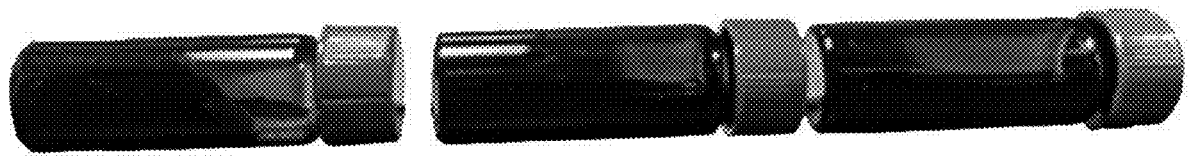
FIG. 9 illustrates pyrolysis oil solubility test results using isophorone and 4-heptanone co-solvents, according to some embodiments of the present disclosure.

FIG. 9 and Table 1 illustrate PPO solubility test results using isophorone and ketone co-solvents, according to some embodiments of the present disclosure. The solubility of isophorone ketones in PPO and resultant change in the PPO's viscosity were tested. Test conditions were as follows: Samples: ~ 3 g each, appropriate volume for a kinematic viscosity measurement; 5 and 10 wt % isophorone; 5 wt % 4-heptanone; 5 wt % 6-undecanone; PPO.

The results from these tests indicate that the 4-heptanone and isophorone had good solubility in the PPO and significantly reduced the PPO viscosity. Referring to FIG. 9, the image compares the 5 wt % samples of isophorone and 4-heptanone with base PPO from BTG Bioliquids. Lower viscosity was exhibited in the PPO/co-solvent mixtures, as indicated by a quicker change in liquid level than that occurring in the neat PPO sample and Table 1. Both formed single-phase solutions with decreased viscosity. The 10 wt % isophorone sample resulted in lower viscosity than the 5 wt % isophorone sample. The 5 wt % 6-undecanone treated PPO sample remained partially undissolved, with higher heating needed to assess the ability to form a single-phase.

Example 4. Fast Pyrolysis Oil Production

Conventional fast pyrolysis process was performed with regen-ag miscanthus biomass supplied by UIUC to generate bio-oil for PPO-SAF production and aqueous phase upgrading. Drying of the biomass was conducted with recycled preheater flue gases using supplemental heat from firing a heater with pyrolysis gas. Residence time in the dryer was 5 to 10 minutes. The pyrolysis was conducted at 450° C. with an operating pressure of ~15-20 psig. Residence time in the pyrolysis unit was ~30 seconds. Miscanthus fast pyrolysis yields as a percent of biomass feed (dry-ash-free basis) are shown in Table 6.

TABLE 6

Miscanthus fast pyrolysis yields as a percent of biomass feed (dry-ash-free basis)

| Pyrolysis component | Product Yields (wt %) |
|---|---|
| Char | 11.64 |
| Gas | 24.12 |
| Total pyrolysis oil | 60.6 |

Example 5. Recycling Solvent

Figure 10:
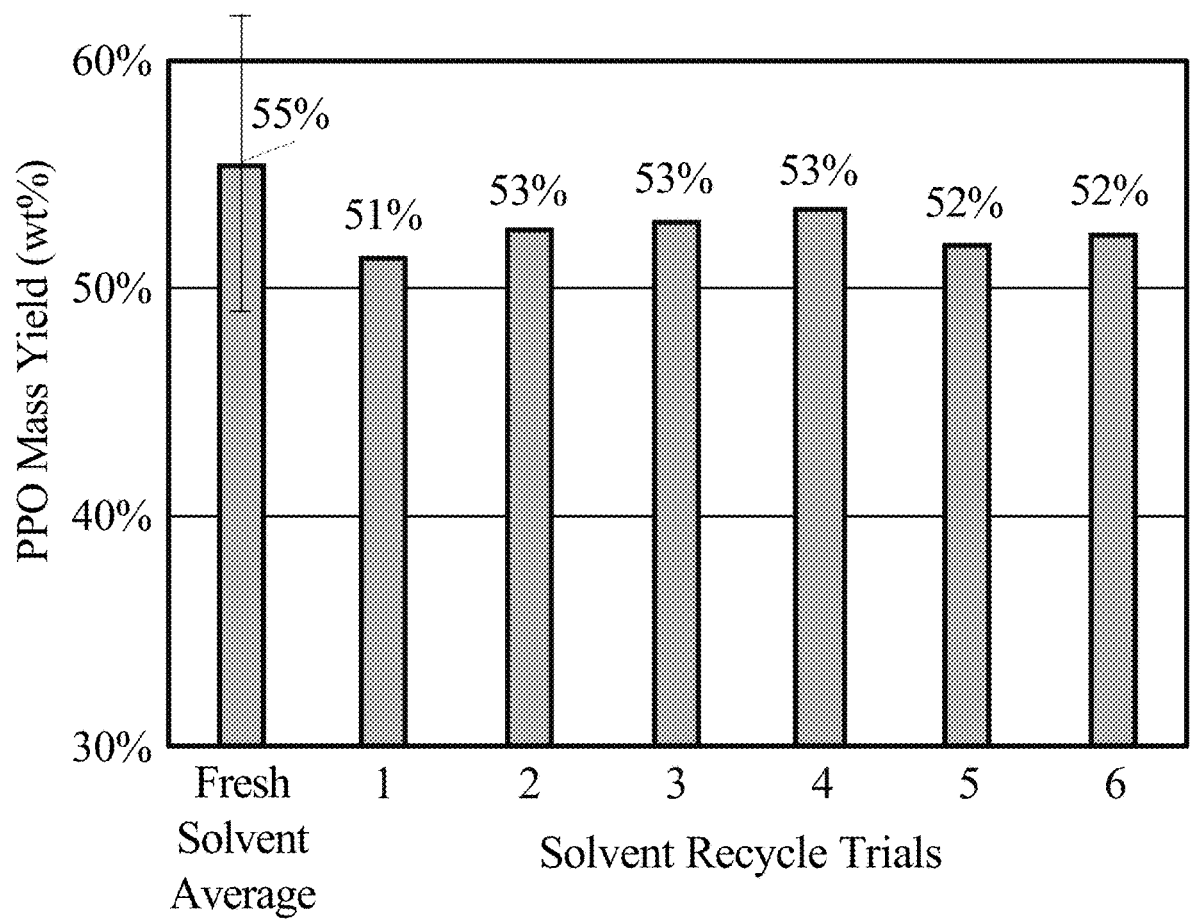
FIG. 10 illustrates PPO production yields with solvent recycle based on validation experiments performed on commercial woody biomass fast pyrolysis oil.

The PPO product and aqueous phase fractions were comparable to those produced from batch processing. PPO batch production runs with solvent recycle were also performed to independently validate commercial woody biomass pyrolysis oil PPO yields and phenolic partitioning, as shown in FIG. 10. FIG. 10 shows PPO production yields with solvent recycle based on experiments performed on commercial woody biomass fast pyrolysis oil.

Example 6. Hydrothermal Carbonization of the Aqueous Phase

Hydrothermal carbonization was performed using Parr high pressure reactor systems that included multi-batch screening 75-mL reactors and a stirred 2-L batch reactor system. Hydrothermal carbonization of the aqueous phase took place at 250° C., autogenous pressure of 580 psig, and a residence time of 1 h. The results show complete conversion of detectable sugars and an acetic acid concentration in the remaining aqueous phase ranging from 5 to 16 wt %. The component and weight analysis of the starting aqueous phase and post-hydrothermal carbonization/oxidation product are included in Tables 7-9.

TABLE 7

Component analysis of the starting aqueous phase.

| Component Mass Fraction | Starting Aqueous Phase |
|---|---|
| C (wt %) | 34% |
| Water (wt %) | 44% |
| Sugar (wt %) | 22% |
| Hydroxy-acetaldehyde (wt %) | 9% |
| 2-Propanone, 1-hydroxy (wt %) | 4% |
| Acetic acid (wt %) | 1.7% |

TABLE 8

Mass yield of products post-hydrothermal carbonization/oxidation.

| Component Mass Fraction | Liquid Post-Hydrothermal | Hydrochar Post-Hydrothermal |
|---|---|---|
| Total mass yield (%) | 36% | 64% |
| C yield (% of starting feed) | 12% | 76% |
| Water yield (% of starting feed) | 60% | 40% |

TABLE 9

Component analysis of liquid product post-hydrothermal carbonization/oxidation.

| Component Mass Fraction | Liquid Post-Hydrothermal |
|---|---|
| C (wt %) | 11% |
| Water (wt %) | 13% |
| Sugar (wt %) | Below detection |
| Acetic acid (wt %) | 5-17% |
| 1-Butanol | 3.6% |
| 1,2-Ethanediol | 0.9% |

Example 7. Short Chain Acid Extraction

Short chain acid extraction was tested at the bench-scale in batch separatory funnels ranging from 100 mL to 1 L, operated at ambient temperature. The acetic acid purification column was operated at or near the boiling point of methyl-tertiary-butyl-ether (MTBE), 55° C., to remove the solvent and produce neat acetic acid. MTBE was added to the post-hydrothermal carbonization aqueous product in a 2:1 ratio to recover acetic acid with a single-pass extraction and non-optimized conditions. No residual acetic acid was observed in the raffinate post extraction.

Example 8. Catalytic Ketonization/Condensation

Short chain acid ketonization was tested in a lab-scale packed bed reactor via gas phase ketonization at the 0.1 gpd scale for 100 h of continuous operation. The ketonization experiment took place in a gas-phase packed bed reactor operating at 350° C., atmospheric pressure, a commercial $ZrO_2$ metal oxide catalyst at a weight hourly space velocity (WHSV) of 3.8 $h^{-1}$. The results show the yields below:

Acetic acid conversion=100%
Liquid mass recovery=90% of expected based on conversion
C3:C9 molar ratio=50-60%.

Example 9. Using Model C3/C9 Alcohols as Co-Solvent Reduces PPO Viscosity

Tests were performed to evaluate reduced PPO viscosity and thermal stability when using a model co-solvent that was produced by aqueous phase acetic acid upgrading. The PPO viscosity data are shown in Table 10.

TABLE 10

Viscosity accelerated aging tests of PPO with addition of 10 wt % co-solvent comprised of model C3/C9 alcohols that can be derived from aqueous phase acetic acid upgrading.

| PPO Sample Type | Viscosity (cP at 40° C.) | Viscosity (cP, 2 h at 100° C.) | Viscosity (cP, 24 h at 100° C.) |
|---|---|---|---|
| PPO from woody biomass | 1665 | N/A | N/A |
| PPO in 10% model C3/C9 alcohols | 359 | 394 | 479 |

Methods

Fast pyrolysis oil and processed pyrolysis oil. Commercial woody biomass fast pyrolysis oil was obtained from BTG Bioliquids. Processed pyrolysis oil (PPO) was produced from this sample using methods described herein. Briefly, room temperature pyrolysis oil and water (10 wt % of the pyrolysis oil) were added to a separatory funnel and shaken for 5-10 min. Butyl acetate (10 wt % of the pyrolysis oil) was then added to the funnel and shaken for 5-10 min. The solution sat for 1-24 h to allow for phase separation before being split into aqueous and organic fractions. The aqueous phase was then extracted twice with butyl acetate (25 wt % of the aqueous phase) and the butyl acetate fractions were combined. The solvent was removed from the organic fraction through rotary evaporation in a water bath up to 75° C. and a pressure down to 50 mbar. The resulting organic fraction is referred to herein as PPO.

PPO co-solvents. PPO was solubilized into various oxygenated co-solvents at different weight loadings and compositions for testing. Co-solvent components included: methanol, isophorone, acetone, isopropanol (IPA), trimethylcyclohexanol (TMCH—OH), and trimethylcyclohexane (TMCH—HC). All co-solvents were obtained from commercial vendors and used as received for experiments.

Acetic acid upgrading to co-solvent. Acetic acid was catalytically converted into a mixed solution comprised predominantly of C3 and Co oxygenates to demonstrate thermochemical aqueous phase organics could be used as a co-solvent for PPO. Experiments were performed with commercial acetic acid that was processed neat in a custom-built catalytic packed bed down flow reactor. The reactor was comprised of a clamshell furnace with internal thermocouple to control the temperature of the catalyst bed, a heat-tape wrapped inlet for pre-heating the reaction mixture, a mass flow controller (Brooks Instruments) for controlling the flowrate of helium gas, a high-pressure liquid chromatography pump for liquid injection, a tube-in-tube heat exchanger for condensing liquids from the reactor effluent, and a knock-out pot for collecting liquid product mixtures. Reactions were performed with a bed temperature of 400° C., a pre-heat zone temperature of 200° C., an acetic acid flowrate of 0.18 mL/min, and a diluent helium gas flowrate of 35 cm$^3$ (STP) min-1. No back-pressure regulation was used, and reactions were at atmospheric pressure. The liquid and gas feeds flowed across 3 g of $ZrO_2$ catalyst (30-50 mesh, Johnson Matthey, calcined at 550° C.). The effluent gas was analyzed by an online non-dispersive infrared detector for concentrations of $CH_4$, CO, $CO_2$, and $O_2$. Liquid samples were evaluated on an Agilent 7890 GC equipped with an HP-5 MS column (30 m×0.25 4 mm), a triple-axis mass spectrometer (MS, Agilent Technologies), and a Polyarc-flame ionization detector (Polyarc-FID). Prior work by our team and others has shown that ketones can be readily hydrogenated to alcohols over metal-supported catalysts. Therefore, no additional hydrogenation tests were performed to convert acetone and isophorone to their corresponding alcohols.

Viscosity and accelerated aging. Dynamic viscosity measurements were performed in a Brookfield viscometer (Model VD2T) fitted with a Wells-Brookfield cone and plate cup with a CPA40Z spindle. The temperature of 40° C. or 50° C. was controlled with a Lauda (Model K2/RD) recirculating bath. The Wells-Brookfield cone and plate cup allows for a small sample size. A sample of 0.5 mL of oil was drawn up into a 1 ml syringe, weighed and added to the cup. The sample was allowed to equilibrate, and the viscosity was measured for 15 min with the average being taken over the last 10 min of the experiment. Accelerated aging bio-oil samples were prepared by heating in a Blue Line oven (Model SW-11TA-1) at 100° C. for the duration indicated.

PPO hydrotreating. Continuous hydrotreating tests were performed with PPO and select co-solvents to validate their sustained performance and target fuel product yields. Hydrotreating reactions were performed in a custom-built catalytic packed bed down flow reactor. Liquids were fed by dual ISCO syringe pumps. Hydrogen gas with 150 ppm $H_2S$ was fed by a mass flow controller. The reactor tube had an internal volume of approximately 60 mL and used a tube-in-tube heat exchanger with compressed air as the working fluid that was heated by a 4-zone electric furnace. After the reactor, a series of tube-in-tube heat exchangers condensed the reaction products by cooling from the reaction temperature. The condensed product was gathered in collection vessels, which were drained once or twice a day for offline analysis by GC-MS and elemental analysis. Parallel automated backpressure valves controlled the system pressure during hydrotreating. Gas sampling ports before and after the reactor route fed gases and non-condensable products to online analytical equipment including an NDIR analyzer and a micro gas chromatograph to monitor reaction performance.

The catalyst was loaded into the reactor in the oxide form and reduced and presulfided in situ. Presulfiding was performed by feeding di-tert-butyl disulfide diluted in decane and hydrogen into the packed bed reactor for approximately 8 hours. The reactor temperature was increased in stages to the final sulfiding temperature of approximately 350-400° C. Hydrotreating runs were performed weight hourly space velocity of 0.2 h$^{-1}$ (liquid flow rate of 2.5 mL/h), $H_2$ flow rate of 175 cm$^3$ (STP) min-1, back pressure held at 1813 psig, and 24 g of $NiMo/Al_2O_3$ catalyst. The catalyst bed was controlled with two thermal zones. The first thermal zone was operated at 250° C. with a 1:2 dilution of SiC. The second thermal zone was operated at 380° C. with no diluent.

The foregoing discussion and examples have been presented for purposes of illustration and description. The foregoing is not intended to limit the aspects, embodiments, or configurations to the form or forms disclosed herein. In the foregoing Detailed Description for example, various features of the aspects, embodiments, or configurations are grouped together in one or more embodiments, configurations, or aspects for the purpose of streamlining the disclosure. The features of the aspects, embodiments, or configurations, may be combined in alternate aspects, embodiments, or configurations other than those discussed above. This method of disclosure is not to be interpreted as reflecting an intention that the aspects, embodiments, or configurations require more features than are expressly recited in each claim. Rather, as the following claims reflect, inventive aspects lie in less than all features of a single foregoing disclosed embodiment, configuration, or aspect. While certain aspects of conventional technology have been discussed to facilitate disclosure of some embodiments of the present invention, the Applicants in no way disclaim these technical aspects, and it is contemplated that the claimed invention may encompass one or more of the conventional technical aspects discussed herein. Thus, the following claims are hereby incorporated into this Detailed Description, with each claim standing on its own as a separate aspect, embodiment, or configuration.

What is claimed is:

1. A method of treating pyrolysis oil to yield a liquid fuel or liquid fuel precursor, the method comprising:
    processing acetic acid to yield one or more alcohols;
    combining the pyrolysis oil with the one or more alcohols to yield a mixture; and
    hydrotreating the mixture to yield the liquid fuel or liquid fuel precursor, wherein:
    processing the acetic acid comprises:
        condensing the acetic acid to yield isopropanone;
        oligomerizing the isopropanone to yield isophorone; and
        hydrogenating the isophorone to yield 3,3,5-trimethylcyclohexanol.

2. The method of claim 1, wherein the pyrolysis oil comprises ≤30 wt % water.

3. The method of claim 1, wherein the pyrolysis oil comprises ≥5 wt % oxygen.

4. The method of claim 1, wherein the mixture comprises between 5 wt % and 95 wt % of the one or more alcohols.

5. The method of claim 4, wherein the one or more alcohols comprise one or more C9 alcohols.

6. The method of claim 5, wherein the one or more alcohols further comprise one or more C3 alcohols.

7. The method of claim 1, wherein the liquid fuel or liquid fuel precursor further comprises one or more of methanol, ethanol, isopropyl alcohol, 1,3,5-trimethylcyclohexane, 1,3,5-trimethylbenzene, 4-heptanol, 6-undecanol, methoxycyclohexane, phenol, 4-propyl-1-cyclohexanol, 1-butanol, 1-octadecanol, and octadecane.

8. The method of claim 1, wherein the pyrolysis oil has a net heat of combustion of ≥15 MJ/kg.

9. The method of claim 1, wherein processing the acetic acid further comprises hydrogenating the isopropanone to yield isopropanol.

10. The method of claim 1, wherein processing the acetic acid further comprises oligomerizing the isopropanone to yield 1,3,5-trimethylbenzene.

11. The method of claim 10, wherein processing the acetic acid further comprises hydrogenating the 1,3,5-trimethylbenzene to yield 1,3,5-trimethylcyclohexane.

12. The method of claim 1, further comprising separating an aqueous component from the pyrolysis oil before combining the pyrolysis oil with the one or more alcohols.

13. The method of claim 12, wherein the aqueous component comprises the acetic acid, and combining the pyrolysis oil with the one or more alcohols comprises recycling the acetic acid.

14. The method of claim 1, wherein the pyrolysis oil is derived from woody biomass.

15. The method of claim 1, wherein the mixture is a single phase mixture.

* * * * *